United States Patent (10) Patent No.: US 9,166,655 B2
Meskens et al. (45) Date of Patent: Oct. 20, 2015

(54) MAGNETIC INDUCTION COMMUNICATION SYSTEM FOR AN IMPLANTABLE MEDICAL DEVICE

(75) Inventors: Werner Meskens, Opwijk (BE); Erika J. Van Baelen, Heverlee (BE); Tony M. Nygard, Terrigal (AU)

(73) Assignee: Cochlear Limited, Macquarie University, NSW (AU)

( * ) Notice: Subject to any disclaimer, the term of this patent is extended or adjusted under 35 U.S.C. 154(b) by 401 days.

(21) Appl. No.: 12/914,619

(22) Filed: Oct. 28, 2010

(65) Prior Publication Data

US 2012/0109256 A1 May 3, 2012

(51) Int. Cl.
*A61N 1/372* (2006.01)
*H04B 5/00* (2006.01)
*A61B 5/07* (2006.01)
*A61N 1/36* (2006.01)
*A61N 1/378* (2006.01)
*H02J 5/00* (2006.01)
*A61B 1/00* (2006.01)
*H02J 7/02* (2006.01)

(52) U.S. Cl.
CPC ............... *H04B 5/0081* (2013.01); *A61B 5/07* (2013.01); *A61N 1/36* (2013.01); *A61N 1/3787* (2013.01); *A61N 1/37223* (2013.01); *H02J 5/005* (2013.01); *H04B 5/0093* (2013.01); *A61B 1/00016* (2013.01); *H02J 7/025* (2013.01)

(58) Field of Classification Search
CPC ............ A61N 1/3787; A61N 1/36032; A61N 1/0541; A61N 1/37211; A61N 1/37223; A61N 1/37217

USPC ................................................ 607/55–57, 60
See application file for complete search history.

(56) References Cited

U.S. PATENT DOCUMENTS

| 5,824,022 | A | 10/1998 | Zilberman et al. |
| 6,505,072 | B1 * | 1/2003 | Linder et al. ........... 607/32 |
| 2007/0116146 | A1 | 5/2007 | Gudnason |
| 2007/0217637 | A1 | 9/2007 | Haenggi et al. |
| 2009/0295543 | A1 | 12/2009 | Kita |
| 2010/0015918 | A1 | 1/2010 | Liu et al. |

(Continued)

FOREIGN PATENT DOCUMENTS

| GB | 2 297 037 A | 7/1996 |
| WO | WO 2004/002572 | 1/2004 |

(Continued)

OTHER PUBLICATIONS

Extended European Search Report in corresponding European Application No. 11835728.4, mailed Oct. 9, 2014, 5 pages.

(Continued)

*Primary Examiner* — Michael Kahelin
*Assistant Examiner* — Minh Duc Pham

(57) ABSTRACT

A communication system for an active implantable medical device. The communication system includes an isolation transformer a coil coupled to the isolation transformer, and first and second communication components each coupled to the isolation transformer such that the first and second communication components are electrically isolated from the coil, and such that the isolation transformer enables the first and second communication components to communicate, via magnetic induction (MI) using the coil, with at least one external component.

21 Claims, 6 Drawing Sheets

(56) References Cited

U.S. PATENT DOCUMENTS

2010/0204756 A1* 8/2010 Aghassian ............... 607/60
2011/0160808 A1* 6/2011 Lyden et al. ............. 607/63

FOREIGN PATENT DOCUMENTS

| WO | WO 2005/055654 | 6/2005 |
| WO | WO 2006/089047 | 8/2006 |
| WO | WO 2006/122836 | 11/2006 |
| WO | 2010093997 A1 | 8/2010 |

OTHER PUBLICATIONS

Office Action in counterpart Chinese Application No. 201180061250.0, mailed Feb. 2, 2015, 10 pages.

Office Action in counterpart Chinese Application No. 201180061250.0, mailed May 14, 2014, 15 pages.

English translation of Chinese Office Action in counterpart Chinese Application No. 201180061250.0, dated May 20, 2015, 3 pages.

* cited by examiner

MAGNETIC INDUCTION COMMUNICATION SYSTEM FOR AN IMPLANTABLE MEDICAL DEVICE

BACKGROUND

1. Field of the Invention

The present invention relates generally to a magnetic induction (MI) communication system, and more particularly to an MI communication system for use in an implantable medical device.

2. Related Art

Medical devices having one or more implantable components, generally referred to herein as implantable medical devices, have provided a wide range of therapeutic benefits to patients (sometimes referred to herein as recipients) over recent decades. Included among implantable medical devices are active implantable medical devices (AIMDs), which are medical devices having one or more implantable components that rely for their functioning upon a source of power other than the human body or gravity, such as an electrical energy source. AIMDs often include an implantable, hermetically sealed electronics module, and a device that interfaces with a patient's tissue, sometimes referred to as a tissue interface. The tissue interface may include, for example, one or more instruments, apparatuses, sensors or other functional components that are permanently or temporarily implanted in a patient. The tissue interface is used to, for example, diagnose, monitor, and/or treat a disease or injury, or to modify a patient's anatomy or to modify a physiological process of a patient.

An implantable medical device may include multiple separate device components that communicate via magnetic induction (MI) over an inductive link in order to transfer power and/or data from one device component to another.

SUMMARY

In one aspect of the present invention, a communication system for an active implantable medical device is disclosed. The communication system comprises an isolation transformer, a coil coupled to the isolation transformer, and first and second communication components each coupled to the isolation transformer such that the first and second communication components are electrically isolated from the coil, and such that the isolation transformer enables the first and second communication components to communicate, via magnetic induction (MI) using the coil, with at least one external component.

In another aspect of the present invention, an implantable component of an implantable medical device is disclosed. The implantable component comprises an isolation transformer, a coil coupled to the isolation transformer, and first and second communication components each coupled to the isolation transformer such that the first and second communication components are electrically isolated from the coil, and such that the isolation transformer enables the first and second communication components to communicate, via the coil, with at least one external component. The isolation transformer, the coil, and the first and second communication components are each part of a circuit equivalent to an LC tank circuit having a single resonant frequency.

In yet another aspect of the present invention, a system comprising first and second external components, and an implantable component. The implantable component comprises an isolation transformer, a coil coupled to the isolation transformer, and first and second communication components each coupled to the isolation transformer such that the first and second communication components are electrically isolated from the coil, and such that the isolation transformer enables the first and second communication components to communicate, using the coil, with the first and second external components via first and second magnetic induction (MI) links, respectively.

BRIEF DESCRIPTION OF THE DRAWINGS

Illustrative embodiments of the present invention are described with reference to the accompanying drawings, in which.

DETAILED DESCRIPTION

Figure 1A:
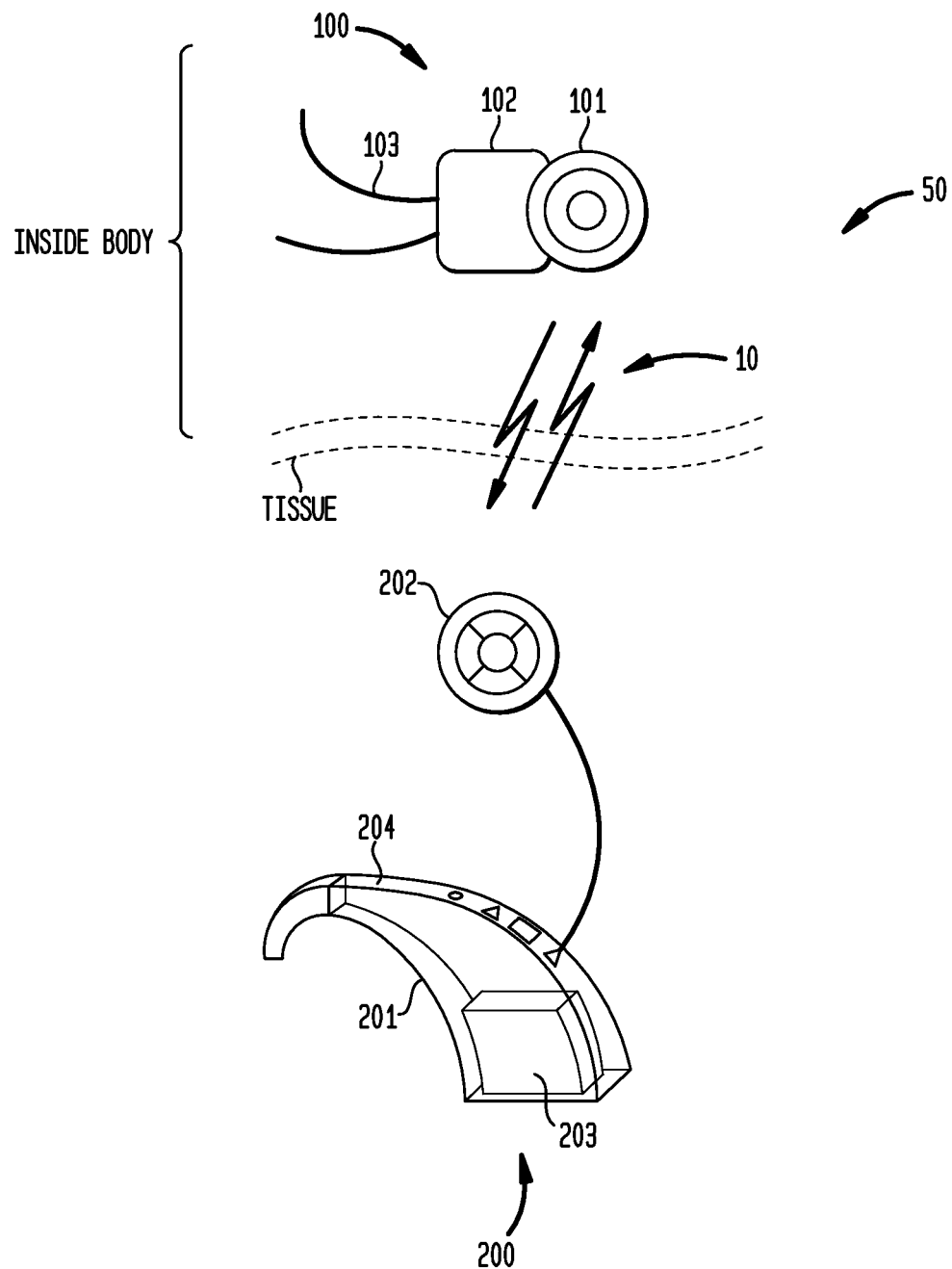
FIGS. 1A and 1B is a schematic diagram illustrating a conventional active implantable medical device (AIMD) using a a closely coupled inductive link to communicate between an implantable component and an external component.

Implantable and external components of an implantable medical device may communicate via a closely coupled magnetic induction (MI) link between an external coil of an external device component and an implantable coil of the implantable device component. As used herein, a "closely coupled MI link" is an MI link having properties of a magnetic "reactive" near field and configured to transfer power and data between device components through body tissue at a distance of approximately 1 to 20 mm. When the closely coupled MI link is modulated in amplitude or frequency, the link may be utilised to transfer data as well as to provide power to the implantable component. A closely coupled MI link may also be referred to herein as a classical power and data link. An implantable hearing prosthesis, which is one example of an implantable medical device, may utilize a closely coupled MI link to communicate between device components, as described below in relation to FIG. 1. A closely coupled MI link may also be referred to herein as a "classical" power and data link.

An implantable component of an implantable medical device that includes an integrated power supply does not require constant communication with an external device component for normal operation. As such, an external component providing data to the implantable component may communicate with the implantable component via another type of MI link, such as a weakly coupled MI radio link. As used herein, a "weakly coupled MI radio link" is an MI link configured to transfer data between device components through body tissue at a range that may extend up to 2 meters. In an implantable hearing prosthesis, for example, that includes an implantable component having an integrated power supply, a Behind-The-Ear (BTE) external component may provide data to the implantable component via a weakly coupled MI radio link. This BTE external component may be smaller and more aesthetically pleasing than a BTE providing power and data to an implantable component. In addition, some implantable medical device recipients may find it beneficial to wirelessly communicate with an implantable device component via a remote control over a weakly coupled MI radio link.

It may be desirable to utilise both a closely coupled MI link to provide power and data to an implantable device component, and a weakly coupled MI radio link to provide data to the implantable component. One approach is to provide a second implantable coil specifically dedicated to communication over the weakly coupled MI radio link. However the placement of the second implanted coil would likely require additional feed-throughs on the casing of the implantable component and increase the total area and volume of the implantable system. Having two separate coils in the implanted device is undesirable from the perspective of complexity, size, and additional feed-throughs. However, difficulties arise when attempting to use a single coil for two different data transmission schemes, including voltage and resonance mismatches.

It is preferable that the weakly coupled MI radio link operates separately from the closely coupled MI link. For example, the weakly coupled MI radio link is preferably electrically isolated from the closely coupled MI link. The circuitry for the MI radio link allows bidirectional data transfers and may be sensitive to over-voltages. More specifically, high voltages received over the closely coupled MI link may damage the weakly coupled MI radio link, thereby reducing reliability.

Aspects of the present invention are generally directed to an MI communication system that enables communication with an implantable device component via both a closely coupled MI link and a weakly coupled MI radio link, each using the same coil of the implantable device component.

Embodiments of the present invention will be described with reference to a particular illustrative example, namely, a cochlear implant system. However, it will be appreciated that the present invention is also applicable to other systems in which it is desirable to communicate power and data via MI. The present invention has particular application in complex medical devices having an implanted power supply intended to be charged inductively, regardless of the particular functionality of the devices. Applications may include, for example, neural stimulation devices, muscle stimulators, drug pumps, monitoring devices, and any other implanted device with power storage. Additionally, the present invention may be applied to various cochlear implant systems, such as a hybrid electrical/acoustic system, an acoustic hearing aid system, a middle ear stimulation system, a bone anchored hearing aid, or any other hearing prosthesis.

The present invention may also find application in both systems having implantable components, and fully external systems. In addition, the weakly coupled MI radio link may be used for various different purposes in conjunction with the present invention. For example, the weakly coupled MI radio link may provide raw or processed acoustic data to a hearing prosthesis; multiple devices may form a network on similar frequencies; or the weakly coupled MI radio link may transfer simple or complex telemetry data in addition to the other data in an uni-directional or bidirectional way. The present invention is not constrained in application or scope by the purpose of the medical device or of the various links. It will be appreciated that the embodiments described herein are for illustrative purposes only, and the scope of the present invention is not limited to any particular embodiment described herein. Many variations and additions are possible within the scope of the present invention.

The present invention has particular application to implantable medical devices, particularly active implantable medical devices (AIMDs), in which closely coupled and weakly coupled MI links are conventionally used. Such AIMDs include, for example, implantable hearing aids, cochlear implants, and the like.

Figure 1B:
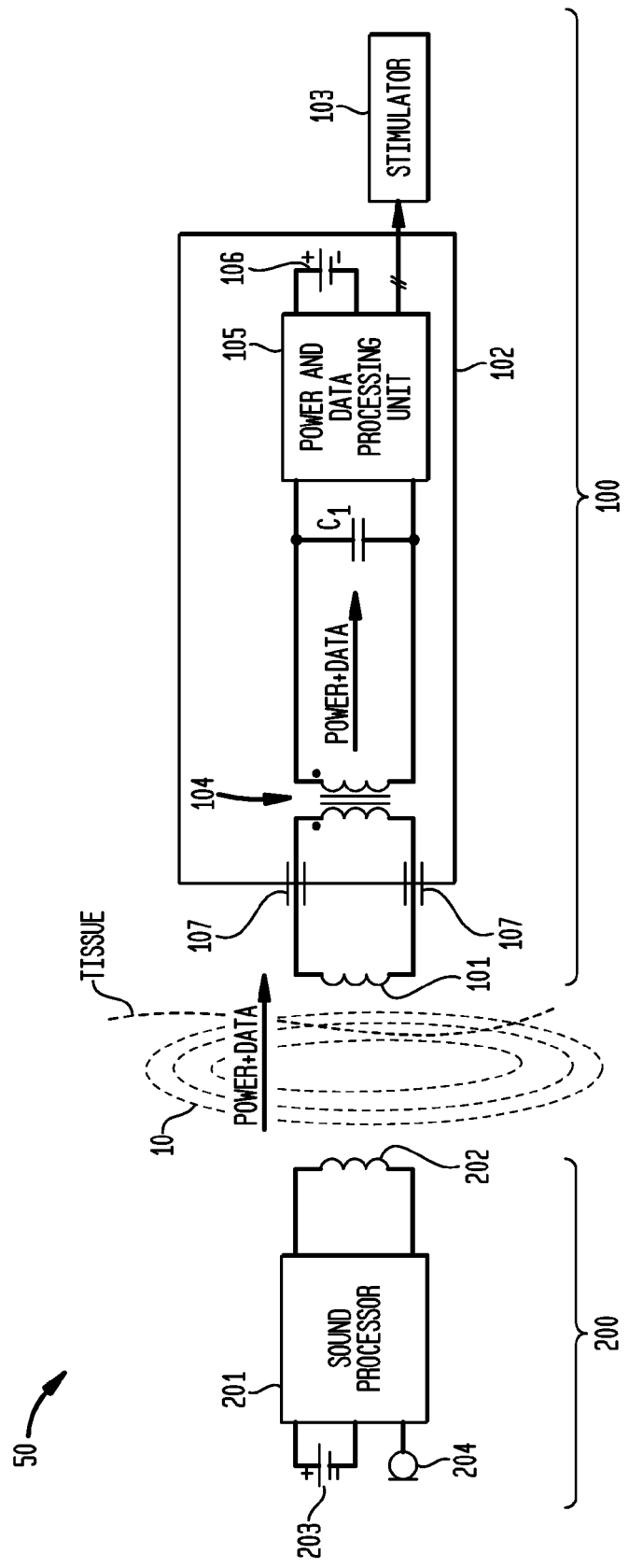

FIGS. 1A and 1B illustrate a conventional AIMD 50 using a closely coupled MI link 10 to communicate between an implantable component 100 and an external component 200. In FIGS. 1A and 1B, AIMD is a cochlear implant. Implantable component 100 includes an implantable coil 101 for receiving and transmitting MI signals, a power and data processing unit 105, a rechargeable power source 106 and a stimulator 103 (in this example, including intra-cochlear electrodes). External device 200 includes an external coil 202 (e.g., a headpiece coil) for inductively communicating with the implanted coil 101, an external power source 203 (e.g., a battery) for providing power to the implantable component 100 or to charge the rechargeable power source 106, an audio input device 204 (e.g., a microphone), and sound processor 201 (e.g., a BTE sound processor) for data transmission over the closely coupled MI link 10.

The closely coupled MI link 10 is established across the tissue (e.g., skin) of a recipient between an implanted coil 101 and an external coil 202, and has a range of approximately 1 to 20 mm. A casing 102 of implantable component 100 is preferably made of titanium. Implantable coil 101 is located outside of casing 102 and connected to other components of implantable component 100 via feed-throughs 107, since the titanium casing would likely decrease the link efficiency if the coil 101 were disposed in the casing. One or more of data and power may be provided to implantable component 100 when closely coupled MI link 10 is modulated in amplitude or frequency.

For safety reasons, implantable coil 101 preferably includes galvanic isolation to avoid unwanted leakage currents through the recipient's tissue in case of implantable coil failure or due to imperfection of the sealing or feed-throughs of implantable component 100. This galvanic isolation may be obtained by implementing an isolation transformer 104, for example a small implantable ring-transformer having primary and secondary windings electrically isolated from each other. The transformer also balances the positive and negative alternating currents, such that the average tissue electrical current flow becomes zero. To obtain maximum efficiency on the power transfer, external coil 202 and implantable coil 101 are placed in resonance at a fixed operation frequency "f1" (e.g., 5 MHz). This resonance frequency may be established by placing capacitors in addition to capacitor $C_1$ in series or parallel with both coils (not shown), making two closely coupled LC-tank circuits.

Figure 2:
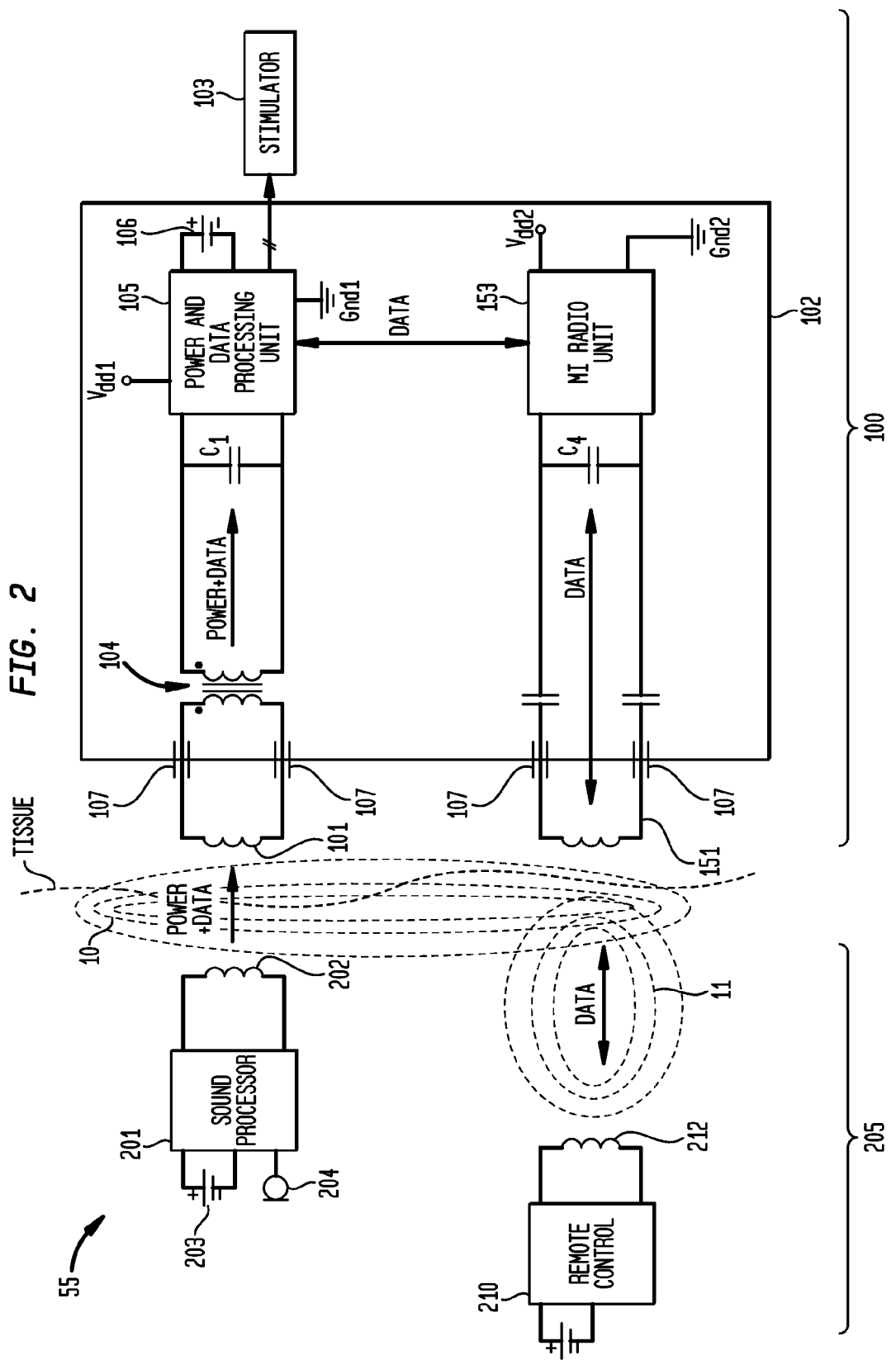
FIG. 2 is a schematic diagram illustrating an AIMD including an implantable device having an MI radio coil for communicating with a remote control via a weakly coupled MI radio link.

To allow implantable component 100 to communicate, via a weakly coupled MI radio link 11, with an external component, located at a distance (e.g., 20 cm to 2 m) from implantable component 100, such as a remote control, implantable component 100 would require additional components. FIG. 2 is a schematic diagram illustrating an AIMD 55 including an implantable device 100 having an MI radio coil 151 for communicating with a remote control 210 via a weakly coupled MI radio link 11. Throughout the drawings, like reference symbols indicate like or similar elements. AIMD 55 includes implantable component 100 and external components 205. External components 205 include remote control 210 and sound processor 201. In addition to MI radio coil 151, implantable component 100 includes an MI radio unit 153 provided to process the MI radio data received via MI radio coil 151. However, as shown in FIG. 2, the presence of the additional MI radio coil 151 would require additional feedthroughs 107 in the casing 102 of implantable component 100 and increase the total area and volume of implantable component 100 (by, e.g., 400 mm² or 1600 mm³).

The MI radio unit 153 should preferably be electrically isolated from the closely coupled MI link 10. If MI radio unit 153 is not electrically isolated from closely coupled MI link 10, resonance frequency mismatches may occur on closely coupled MI link 10 and weakly coupled MI radio link 11, resulting in decreased link efficiencies. Additionally, DC biasing misalignment at the input pins of the power and data processing unit 105 and the MI radio unit 153 may occur due to different power supplies (Vdd voltages) of units 105 and 153. The DC biasing voltage is often half of the Vdd voltage to allow maximum voltage swing of the positive and negative alternating input voltages. Misalignment causes early saturation and signal distortion, and often invokes increased power consumption. Further, the closely coupled MI link 10 often generates voltages higher than 5V, and such high voltages ("over-voltages") could damage MI radio unit 153 if it is not electrically isolated from the closely coupled MI link 10.

Figure 3:
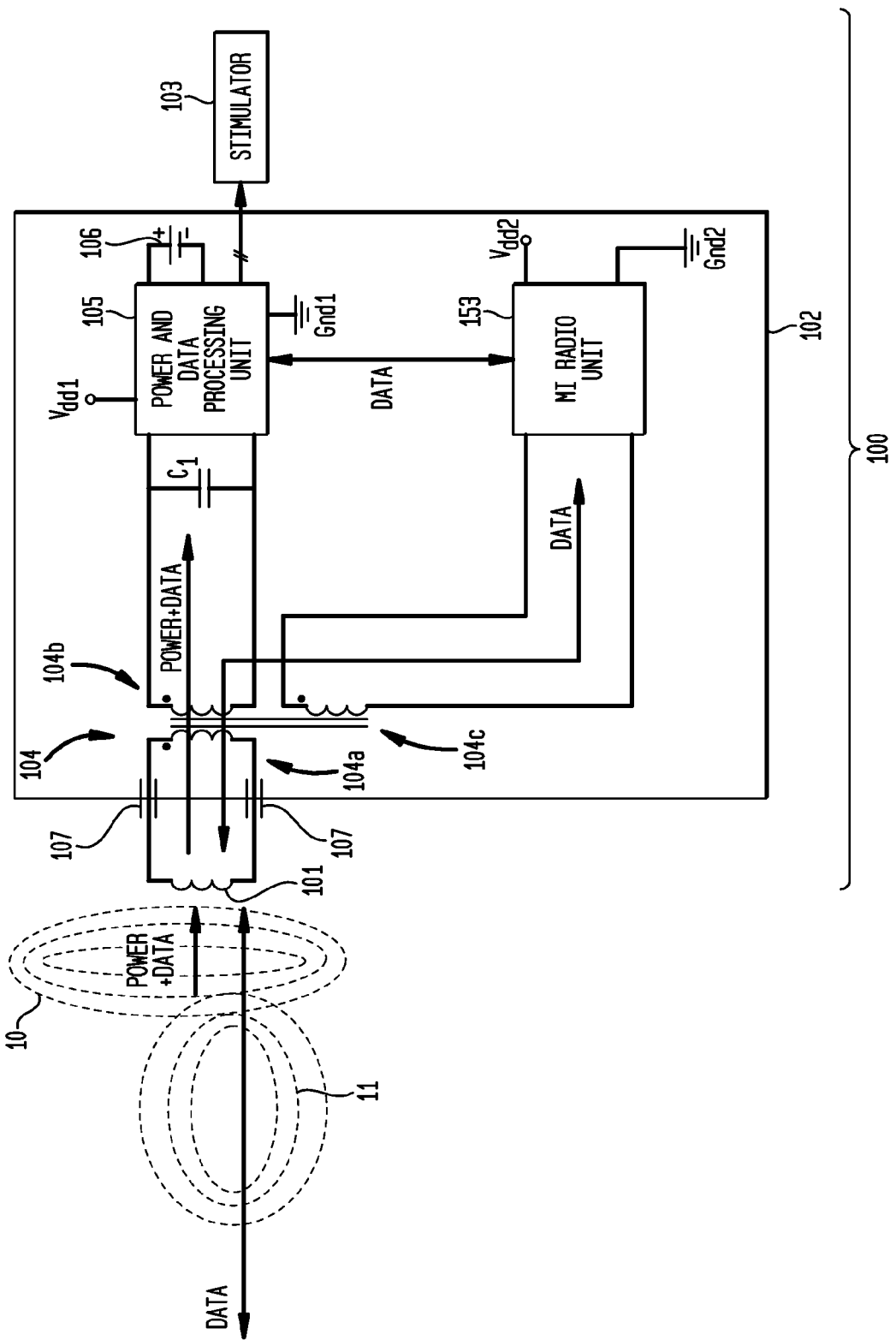
FIG. 3 is a schematic diagram of an MI system for an implantable medical device in accordance with embodiments of the present invention.

FIG. 3 is a schematic diagram of an MI system for an implantable medical device in accordance with embodiments of the present invention. As illustrated in FIG. 3, implantable component 100 includes a single implantable coil 101 positioned outside of casing 102 for forming both a closely coupled MI link 10 with an external component (not shown) and a weakly coupled MI radio link 11 with another external component (not shown). As there is only one coil located outside implant casing 102, no additional feed-throughs 107 are required. Implantable coil 101 is connected to isolation transformer 104. As illustrated in FIG. 3, isolation transformer 104 comprises a first winding 104a, a second winding 104b, and a third winding 104c. First winding 104a is coupled to implantable coil 101 and includes N1 turns. Second winding 104b is coupled to power and data processing unit 105 and third winding 104c is coupled to MI radio unit 153. Second winding 104b includes N2 turns and third winding 104c has N3 turns. Second and third windings 104b and 104c are inductively coupled with first winding 104a. When implantable component 100 is communicating with an external device via a closely coupled MI link 10, power and data signals are received through implanted coil 101, communicated inductively between windings 104b and 104a, and then input to power and data processing unit 105.

Closely coupled MI link 10 should be operated at a first frequency f1. When implantable component 100 receives signals from an external device via weakly coupled MI radio link 11, MI radio signals are received through implanted coil 101, communicated inductively between windings 104a and 104c, and then input to MI radio unit 153. Outgoing MI radio data from implantable component 100 may be output through winding 104b or 104c. To use winding 104b for outgoing MI radio data, additional transmitter driver circuitry (e.g., a level shifter) is required in the power and data processing unit 105. In alternative embodiments, MI radio unit 153 may be connected winding 104b like power and data processing unit 105 such that MI radio unit 153 may output MI radio data via winding 104b. The external device may be a BTE component, a remote control, or another implantable device such as a bilaterally disposed hearing implant or an implantable microphone. Weakly coupled MI radio link 11 should be operated at a second frequency f2 different than first frequency f1. If first and second frequencies f1 and f2 were the same, then in some embodiments the stronger closely coupled MI link may interfere with the signals of weakly coupled MI radio link 11.

Isolation transformer 104 provides galvanic isolation in case of a failure of implantable coil 101, and balances the currents (equal positive and negative alternating tissue currents). Isolation transformer 104 electrically isolates the internal circuitry of implantable component 100 from implantable coil 101, and thereby electrically isolates that internal circuitry from the tissue of a recipient when implantable component 100 is implanted in the recipient. Additionally, isolation transformer 104 acts as a coupler/splitter element for MI radio unit 153 and power and data processing unit 105. Windings 104a, 104b and 104c are electrically isolated from one another and accordingly substantially prevent the issues and disadvantages of DC biasing and over-voltages noted above.

It will be appreciated that implantable component 100 may be constructed such that either one of weakly coupled MI radio link 11 and closely coupled MI link 10 may be unidirectional or bidirectional. As such, each of power and data processing unit 105 and MI radio unit 153 may be a receiver, transmitter or both. As used herein, a "communication component" may be a receiver, transmitter or both as appropriate, and may be configured to communicate data and/or power as appropriate.

The number of windings of N2 (e.g. 16) are preferably chosen much larger than N1 (e.g. 4) To achieve an optimal rectified voltage on power and data processing unit 105, the number of turns N2 of winding 104b is preferably much larger than the number of turns N1 of winding 104a. For example, winding 104b may include sixteen turns (i.e., N2 is equal to sixteen) and winding 104a may include four turns (i.e., N1 is equal to four). In this way, even when a relatively low power signal is provided over closely coupled MI link 10, the rectified voltage received by power and data processing unit 105 may still be sufficiently high to start implantable component 100 and to supply power to the battery charger of implantable component 100. A relatively low amount of power received closely coupled MI link 10 is often caused by a relatively low coupling factor between an external coil and implantable coil 101 due to skin flap thickness.

The winding ratio of isolation transformer 104 will virtually increase or decrease the antenna inductance $L_{IMPLANT}$ of implanted coil 101. The inductance on the primary $L_{IMPLANT}$ seen at the secondary leads of the transformer (i.e., the leads connected to winding 104b) is equal to $L_{IMPLANT} \times (N2/N1)^2$. This is important for determining the capacitor values for obtaining LC tank resonance. Generally, the resonant frequency $f_{res}$ is equal to $1/(2\pi\sqrt{(L*C)})$.

The number of turns N3 of winding 104c is preferably chosen to be lower than the number of turns N2 of winding 104b. Winding 104c may have four turns (i.e., N3 is equal to four) and winding 104b may include sixteen turns (i.e., N2 is equal to sixteen). By providing winding 104b with more turns than winding 104c (i.e., N3<N2), MI radio unit 153 may be implemented on a low-voltage application specific integrated circuit (ASIC) and powered by a lower supply voltage $V_{DD2}$ than power and data processing unit 105. As one example, 180 nm technology is supplied at a supply voltage of 1.4V to 1.8V. By using a low-voltage ASIC connected to a winding 104c having fewer turns N3 than winding 104b (yielding a relatively high turn ratio N2/N3), the influence of the input capacitance of MI radio unit 153 becomes less critical on the LC resonance tank constituted by $L_{IMPLANT}$ and $C_1$ ($X_{cap\ viewed\ at\ N2} = X_{cap\ on\ N3}/(N2/N3)^2$).

The input of MI radio unit 153 is typically a very sensitive small-signal input with high gain amplification (e.g., inputs of 40 dBμV are typical). Therefore, the number of turns N3 of winding 104c of transformer 104 can be chosen such that over-voltage protection of MI radio unit (ASIC) 153 inputs does not clip the signal emanating from closely coupled MI power link 10 (e.g., a relatively large 5 MHz signal) for recharging the implantable battery. Also, the number of turns N3 of winding 104c can be chosen such that MI radio unit (ASIC) 153 does not fail due to over-voltages of closely coupled MI link 10. In general, the turn ratios of windings 104b and 104c should be chosen such that N3<N2 (e.g., N3 equals two turns and N2 equals sixteen turns).

In certain embodiments, implantable component 100 is configured such that it forms the equivalent of an LC tank circuit (i.e., a resonant circuit) having a single resonant frequency. In such embodiments, all of the capacitance and inductance of the circuitry forming implantable component 100, including isolation transformer 104 and coil 101, form part of the LC tank circuit. Additionally, in certain embodiments, AIMD 55 may include an additional implantable component configured to communicate with at least one external component via a closely coupled MI link and with implantable component 100 via a weakly coupled MI radio link, as described above in relation to implantable component 100.

Figure 4:
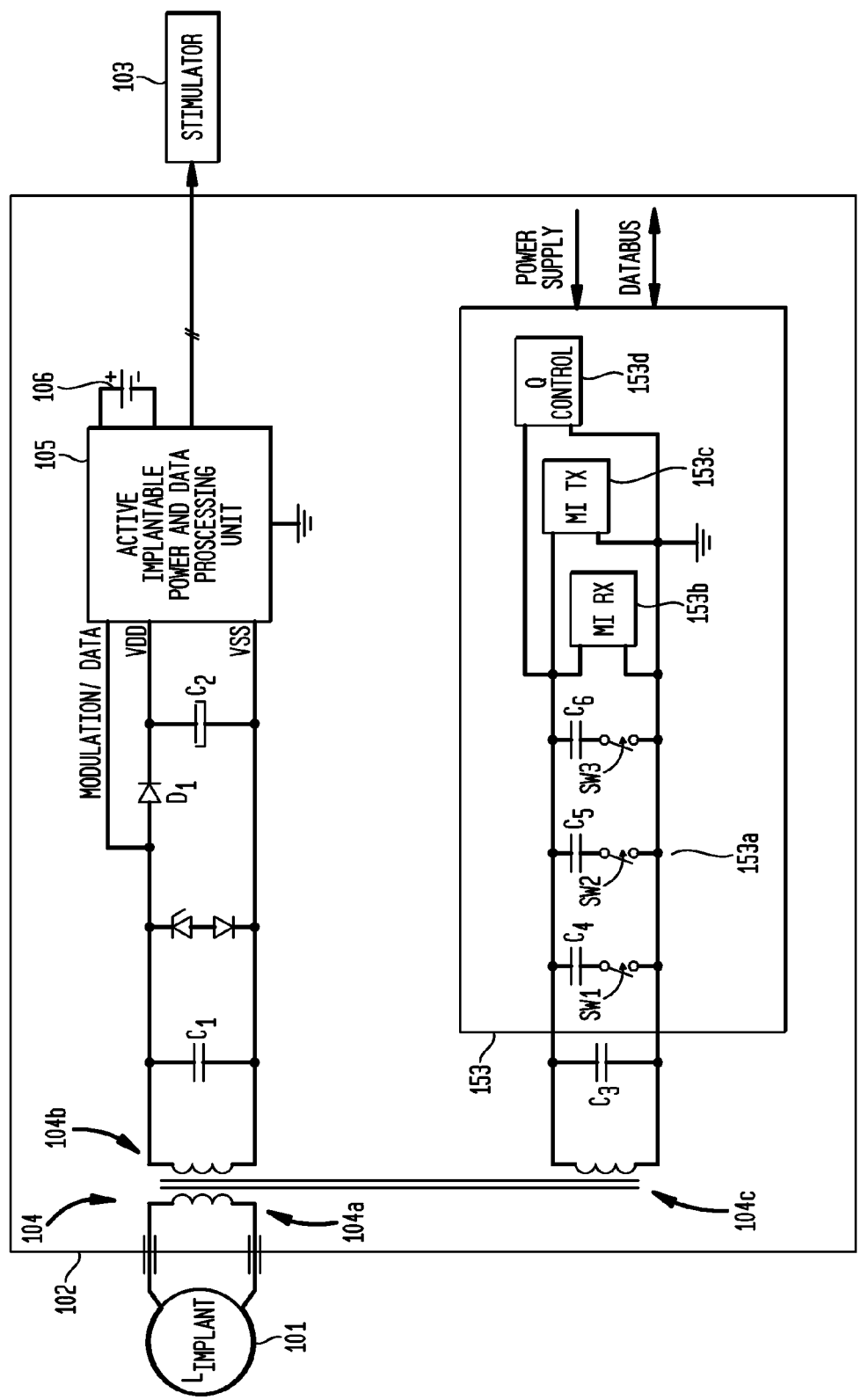
FIG. 4 is a schematic diagram of the implantable component illustrated in FIG. 3 with additional circuitry for frequency and Q-factor control.

FIG. 4 is a schematic diagram of implantable component 100 illustrated in FIG. 3 with additional circuitry for frequency and Q-factor control. As shown in FIG. 4, the resonant frequency of implantable component 101 can be controlled by selection of additional capacitors 153a. Additional capacitors 153a include capacitors C4, C5 and C6, which may be selected using MOSFET switches SW1, SW2 and SW3, respectively, to change the resonant frequency of the system. Changing the resonant frequency can also be accomplished through the selection of additional inductors replacing capacitors C4, C5 and C6. In a broader sense, the resonance at frequencies f1 or f2 may be obtained by placing additional capacitors or inductors in series, parallel, or series and parallel near first winding 104a, second winding 104b or third winding 104c. However, in preferred implementations, only capacitors are used, and they may be distributed over all windings.

The resonant frequency of implantable component 100 may be controlled such that the resonant frequency is equal to or near (i.e., within a few percentage points of) frequency f1 when implantable component 100 is communicating over closely coupled link 10. Similarly, the resonant frequency of implantable component 100 may be controlled such that the resonant frequency is equal to or near frequency f2 when implantable component 100 is communicating over weakly coupled MI radio link 11.

In certain embodiments, a processor, such as power and data processing unit 105, may determine when to change the resonant frequency, and cause the change to be made. In some embodiments, the processor may change the resonant frequency of implantable component 100 in accordance with a time division multiple access (TDMA) scheme so that coil 101 may be used to communicate over multiple frequencies. In other embodiments, implantable component 100 may use a signal protocol arbiter to determine what frequency is required by an incoming signal. For example, communication with implantable component 100 use a standard protocol in which each signal includes a flag indicating the frequency required by the signal. The processor may use that flag to determine what resonant frequency should be established for implantable component 100. Implantable component 100 can only be tuned to one resonant frequency at a time. As such, implantable component 100 cannot simultaneously receive signals at frequencies f1 and f2.

The presence of a selectable resistor bank 153d or a variable resistor allows the quality factor (Q-factor) of the coil antenna tank circuit to be adapted to the optimum link bandwidth. Depending on modulation, line coding, compression and data rate, a minimum system bandwidth is required. Changing capacitance or resistance to adjust the antenna tank circuit characteristics may be done by specific instructions or in an automated way by means of a processing unit (not shown). When automated, an algorithm providing the most optimal system settings is required. Any frequency or bandwidth drift due to external factors would could be compensated for by the algorithm. As illustrated in FIG. 4, MI radio unit 153 includes a tuning capacitor $C_3$, an MI receiver 153b, an MI transmitter 153c, each connected to winding 104c. MI receiver 153b is configured to receive signals provided over weakly coupled MI radio link 11 and an MI transmitter 153c is configured to output signals over weakly coupled MI radio link 11. Additionally, as illustrated in FIG. 4, implantable component 100 includes a multiple diodes (including a diode D1) and a capacitor C2 connected to winding 104b.

Figure 5:
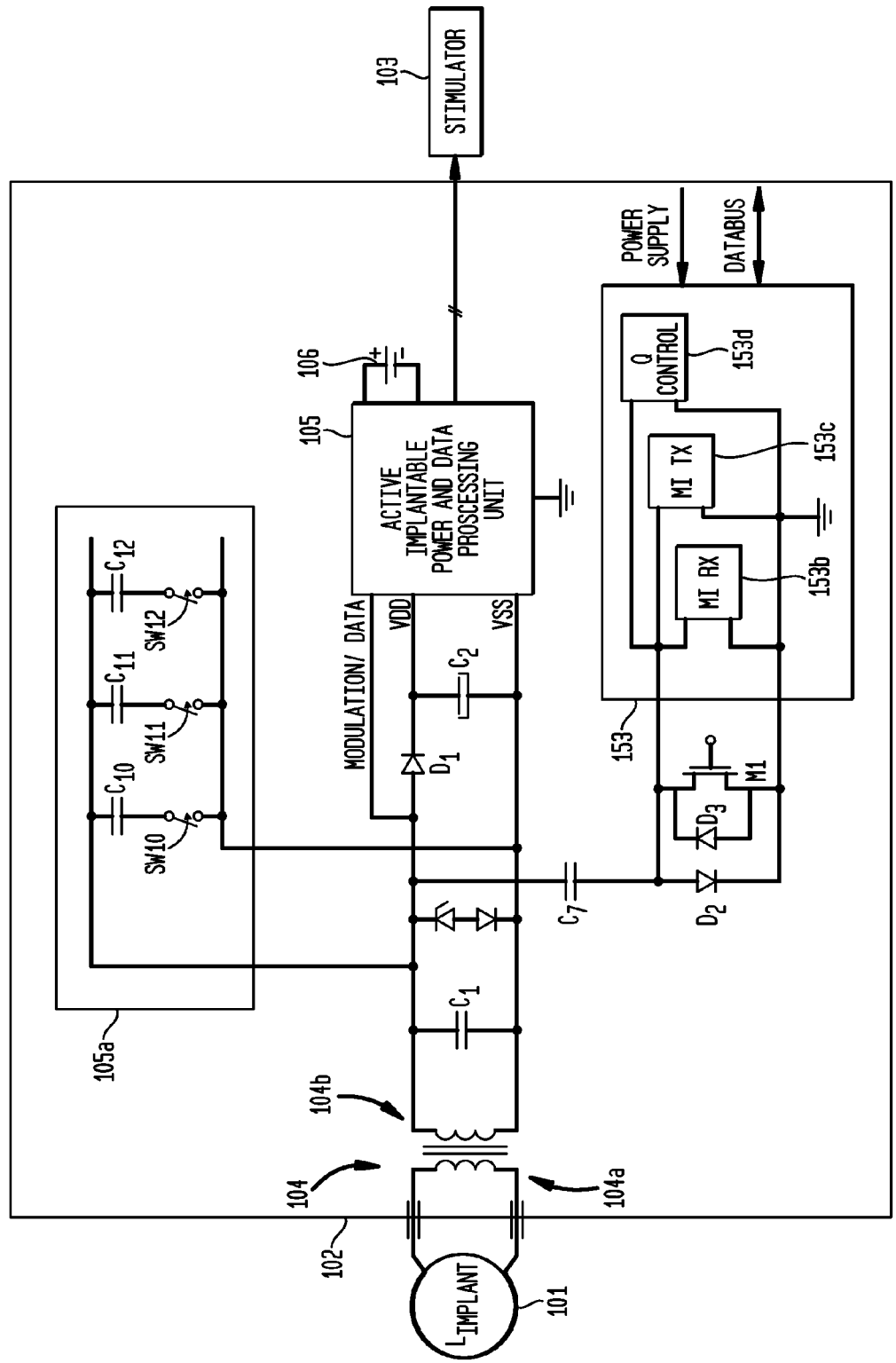
FIG. 5 is a schematic diagram of an alternative implantable component having a single implantable coil disposed outside of the casing of the implantable component and connected to an isolation transformer.

FIG. 5 is a schematic diagram of an alternative implantable component 100 having a single implantable coil 101 disposed outside of casing 102 and connected to an isolation transformer 104. MI radio unit 153 is capacitively coupled, via capacitor $C_7$, to secondary winding 104b of transformer 104. However, a low-voltage ASIC (which MI radio unit may be in some embodiments) capacitively coupled to winding 104b may significantly detune the resonance frequency or decrease the power transfer efficiency of closely coupled MI link 10 by clipping or saturation effects. An imprudent design may also destroy the lower-voltage ASIC because voltages and transients of closely coupled MI link 10 could easily rise above 20 Volts peak. Therefore, overvoltage protection is obtained from diodes D2 and D3 (intrinsic to MOSFET switch M1).

For a closely coupled MI link 10, diodes D2 and D3 are conducting and capacitor $C_7$ will virtually be placed parallel to capacitor C1. For smaller signals, such as incoming signals over a weakly coupled MI radio link 11, both diodes D2 and D3 will be non-conducting and the resonance frequency would be higher. However, the change in resonance frequency can also be compensated for or introduced by using a selectable capacitor bank 105a, if necessary. The presence of a selectable capacitor bank 105a allows the implantable antenna to be adapted to the most optimum link efficiency, whether each link operates at the same or a different modulated carrier frequency. Implantable component 100 may also include one or more radio frequency (RF) current/voltage measurement units for capacitor bank adjustment and leakage current measurement. Leakage current is detrimental in that is it could generate anodic and cathodic tissue reactions.

The benefits of using different or similar frequencies can be related to regulatory aspects applicable to emission levels. Higher levels are allowed for inductive power links at 13.56 MHz (ISM band). It is not preferred to use a weakly coupled MI radio link over this widely accepted ISM-frequency because of possible interference in the presence of, for example, RF-ID, industrial induction RF heaters, etc. Reliable weakly coupled MI radio links often use other frequencies. The benefit of using similar frequencies is that it may allow system or hardware simplification. The use of a selectable capacitor bank becomes optional in such an arrangement.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents. All patents and publications discussed herein are incorporated in their entirety by reference thereto.

What is claimed is:

1. An implantable communication system for an active implantable medical device comprising:
    an isolation transformer;
    a coil coupled to said isolation transformer;
    a first communication component coupled to said isolation transformer so as to receive power and data from a first external component over a closely coupled magnetic induction (MI) link operating at a first frequency and formed between the coil and the first external component; and
    a second communication component coupled to said isolation transformer so as to receive data from a second external component over a weakly coupled MI link formed between the coil and the second external component, wherein the weakly coupled MI link operates at a second frequency that is different from the first frequency of the closely coupled MI link.

2. The system of claim 1, wherein said isolation transformer comprises:
    a first winding coupled to said coil and a second winding coupled to the first and second communication components.

3. The system of claim 1, wherein said isolation transformer comprises:
    a first winding coupled to said coil;
    a second winding coupled to said first communication component; and
    a third winding coupled to said second communication component.

4. The system of claim 1, wherein said isolation transformer, said coil, and said first and second communication components are each part of a circuit that is equivalent to an LC tank circuit having a single resonant frequency.

5. The system of claim 4, further comprising:
    circuitry configured to change the resonant frequency of the circuit such that the resonant frequency is alternatively close to the first frequency or the second frequency.

6. The system of claim 5, further comprising:
    a processor configured to use a signal arbiter to dynamically determine which resonant frequency to which the circuit should be tuned.

7. An implantable component of an implantable medical device comprising:
    an isolation transformer;
    a coil coupled to said isolation transformer;
    first and second communication components each coupled to said isolation transformer such that said first and second communication components are electrically isolated from said coil, and such that said isolation transformer enables said first and second communication components to communicate, via said coil, with a first external component, wherein said isolation transformer, said coil, and said first and second communication components are each part of a circuit equivalent to an LC tank circuit having a single resonant frequency,
    wherein said first communication component is configured to receive power and data from the first external component over a closely coupled MI link operating at a first frequency and formed between the coil and the first external component and wherein said second communication component is configured to receive data from a second external component over an MI radio link operating at a second frequency that is different than the closely coupled MI link.

8. The system of claim 1, wherein the closely coupled MI link is configured to charge a rechargeable power source associated with the first communication component.

9. The implantable component of claim 7, wherein said isolation transformer comprises:
    a first winding connected to said coil;
    a second winding connected to said first communication component; and
    a third winding connected to said second communication component,
    wherein said first, second, and third windings are electrically isolated from one another.

10. The implantable component of claim 9, wherein said first communication component is configured to output, over said MI radio link via said second winding, signals received from said second communication component.

11. The implantable component of claim 9, wherein said second communication component is configured to communicate with said at least one external component over said MI radio link via said third winding.

12. The implantable component of claim 9, wherein said second communication component is a low-voltage integrated circuit (IC) configured to send and receive data signals over said MI radio link via said third winding.

13. The implantable component of claim 7, further comprising:
    circuitry configured to change the resonant frequency of the LC tank circuit such that the resonant frequency is alternatively close to the first frequency or the second frequency.

14. The implantable component of claim 13, further comprising:
    a processor configured to use a signal arbiter to dynamically determine which resonant frequency to which the LC tank circuit should be tuned.

15. A system comprising:
    first and second external components; and
    an implantable component comprising:
    an isolation transformer;
    a coil coupled to said isolation transformer; and
    a first communication component coupled to said isolation transformer so as to receive power and data from the first external component over a closely coupled magnetic induction (MI) link operating at a first frequency and formed between the coil and the first external component; and
    a second communication component coupled to said isolation transformer so as to receive data from the second external component over a weakly coupled MI link formed between the coil and the second external component, wherein the weakly coupled MI link operates at a second frequency that is different from the first frequency of the closely coupled MI link.

16. The system of claim 15, wherein said system is a cochlear implant.

17. The system of claim 16, wherein said implantable component comprises:
    a plurality of electrodes, wherein said first communication component is configured to provide electrical stimulation to a recipient via said electrodes.

18. The system of claim 15, wherein said isolation transformer comprises:
- a first winding coupled to said coil;
- a second winding coupled to said first communication component; and
- a third winding coupled to said second communication component.

19. The system of claim 15, wherein said isolation transformer, said coil, and said first and second communication components are each part of an LC tank circuit having a single resonant frequency.

20. The system of claim 19, further comprising:
- circuitry configured to change the resonant frequency of the LC tank circuit such that the resonant frequency is alternatively close to the first frequency or the second frequency.

21. The system of claim 20, further comprising:
- a processor configured to use a signal arbiter to dynamically determine which resonant frequency to which the LC tank circuit should be tuned.

* * * * *